(12) United States Patent
Ekwuribe et al.

(10) Patent No.: US 6,610,739 B2
(45) Date of Patent: Aug. 26, 2003

(54) 6-METHOXY-2-NAPHTHYLACETIC ACID PRODRUGS

(75) Inventors: Nnochiri Nkem Ekwuribe, Cary, NC (US); Jennifer A. Riggs, Raleigh, NC (US)

(73) Assignee: Nobex Corporation, Durham, NC (US)

( * ) Notice: Subject to any disclaimer, the term of this patent is extended or adjusted under 35 U.S.C. 154(b) by 0 days.

(21) Appl. No.: 10/224,823

(22) Filed: Aug. 21, 2002

(65) Prior Publication Data
US 2003/0027861 A1 Feb. 6, 2003

Related U.S. Application Data

(62) Division of application No. 10/223,426, filed on Aug. 19, 2002, which is a division of application No. 09/698,594, filed on Oct. 27, 2000, now Pat. No. 6,436,990

(60) Provisional application No. 60/161,864, filed on Oct. 27, 1999.

(51) Int. Cl.⁷ ...................... A61K 31/235; A61K 31/24
(52) U.S. Cl. ...................................... 514/532; 514/540
(58) Field of Search ................................. 514/532, 540

(56) References Cited

U.S. PATENT DOCUMENTS

| | | | |
|---|---|---|---|
| 3,883,662 A | 5/1975 | Henzl et al. ............... 424/333 |
| 3,904,682 A | 9/1975 | Fried et al. ................ 260/520 |
| 3,978,116 A | 8/1976 | Fried et al. .......... 260/500.5 H |
| 4,009,197 A | 2/1977 | Fried et al. ............. 260/473 F |
| 4,061,779 A | 12/1977 | Lake et al. ................ 424/331 |
| 4,246,164 A | 1/1981 | Felder et al. .......... 260/501.17 |
| 4,246,193 A | 1/1981 | Holton .................. 260/501.17 |
| 4,268,442 A | 5/1981 | Kondo et al. ............ 260/326.2 |
| 4,270,004 A | 5/1981 | Rose et al. ................. 568/314 |
| 4,327,022 A | 4/1982 | Bailey ..................... 260/239 B |
| 4,328,356 A | 5/1982 | Giordano et al. ............. 560/56 |
| 4,420,639 A | 12/1983 | Lake et al. .................. 568/328 |
| 4,423,244 A | 12/1983 | Cannata et al. ............. 562/466 |
| 4,501,913 A | 2/1985 | Giordano et al. ........... 560/100 |
| 4,515,811 A | 5/1985 | Holton ....................... 514/554 |
| 4,542,237 A | 9/1985 | Schloemer ................. 562/466 |
| 4,546,201 A | 10/1985 | Piccolo et al. ............... 562/401 |
| 4,550,191 A | 10/1985 | Castaldi et al. ............... 560/56 |
| 4,608,441 A | 8/1986 | Citterio et al. .............. 562/466 |
| 4,611,088 A | 9/1986 | Ohara et al. ................ 562/466 |
| 4,654,438 A | 3/1987 | Schloemer .................. 562/496 |
| 4,661,524 A | 4/1987 | Thomson et al. ........... 514/682 |
| 4,661,525 A | 4/1987 | Grazioso et al. ............ 518/714 |
| 4,670,586 A | 6/1987 | Yabe et al. .................. 562/466 |
| 4,670,603 A | 6/1987 | Piccolo et al. .............. 568/319 |
| 4,709,089 A | 11/1987 | Shimizu et al. ............. 562/466 |
| 4,723,033 A | 2/1988 | Erickson ..................... 560/56 |
| 4,724,102 A | 2/1988 | Cannata et al. ........ 260/501.15 |
| 4,814,494 A | 3/1989 | Shimizu et al. ............. 562/419 |
| 4,851,426 A | 7/1989 | Ladkani et al. ............. 514/420 |
| 4,865,770 A | 9/1989 | Piselli ....................... 562/402 |
| 4,922,009 A | 5/1990 | Villa et al. ................. 562/466 |
| 4,937,379 A | 6/1990 | Giordano et al. ........... 562/493 |
| 4,970,336 A | 11/1990 | Yoshioka et al. ........... 562/460 |
| 5,004,832 A | 4/1991 | Castaldi et al. ............. 562/490 |
| 5,068,458 A | 11/1991 | Dales et al. ................ 568/634 |
| 5,132,466 A | 7/1992 | Dales et al. ................ 568/631 |
| 5,145,993 A | 9/1992 | Kim et al. .................. 562/466 |
| 5,179,208 A | 1/1993 | Kim et al. .................. 548/230 |
| 5,200,555 A | 4/1993 | Kessels ...................... 562/401 |
| 5,202,495 A | 4/1993 | Callander ................... 568/315 |
| 5,223,640 A | 6/1993 | Tafesh et al. ............... 562/466 |
| 5,225,603 A | 6/1993 | Aslam et al. ............... 568/315 |
| 5,248,815 A | 9/1993 | Paradies .................... 562/496 |
| 5,278,333 A | 1/1994 | Loosen et al. ................ 562/52 |
| 5,306,833 A | 4/1994 | Vallejos et al. ............... 549/79 |
| 5,426,243 A | 6/1995 | Lecouve ..................... 568/737 |
| 5,539,000 A | 7/1996 | Leonard ..................... 514/682 |
| 5,600,009 A | 2/1997 | Fritch et al. ................ 568/318 |
| 5,621,000 A | 4/1997 | Arena et al. ................ 514/441 |

(List continued on next page.)

FOREIGN PATENT DOCUMENTS

| | | | |
|---|---|---|---|
| DE | 2 051 012 | 4/1972 | .......... C07C/61/28 |
| EP | 0974584 | 1/2000 | ......... C07D/213/06 |
| FR | 2 060 332 | 4/1970 | .......... A61K/27/00 |
| WO | WO 94/04484 | 3/1994 | ......... C07C/229/42 |
| WO | WO 94/12463 | 6/1994 | ......... C07C/203/04 |
| WO | WO 95/30641 | 11/1995 | ......... C07C/203/04 |
| WO | WO 97/31654 | 9/1997 | .......... A61K/45/06 |

OTHER PUBLICATIONS

Benoni, et al., *Plasma Concentrations and Pharmacokinetic Parameters of Nitrofenac Using a Simple and Sensitive HPLC Method,* Journal of Pharmaceutic Sciences, vol. 84, No. 1, Jan. 1995 (pp. 93–95).

(List continued on next page.)

*Primary Examiner*—Rebecca Cook
(74) *Attorney, Agent, or Firm*—Myers Bigel Sibley & Sajovec; William A. Barrett, Esq.

(57) ABSTRACT

The present invention provides compositions useful for the treatment of inflammation in humans, and related methods of treatment for the same. In one embodiment the composition is

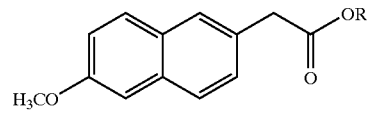

In another embodiment, the composition is

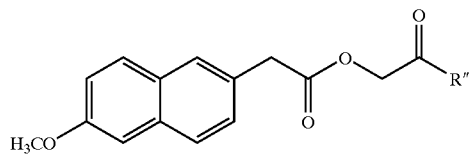

Additional alternative embodiments are R or R″ that are therapeutic moieties.

20 Claims, 2 Drawing Sheets

U.S. PATENT DOCUMENTS

| | | | |
|---|---|---|---|
| 5,695,774 A | 12/1997 | Clark | 424/464 |
| 5,700,947 A | 12/1997 | Soldato | 548/491 |
| 5,703,073 A | 12/1997 | Garvey et al. | 514/226.5 |
| 5,741,938 A | 4/1998 | Belmont | 568/322 |
| 5,750,764 A | 5/1998 | Marais et al. | 560/56 |
| 5,750,793 A | 5/1998 | Cannata et al. | 568/315 |
| 5,756,851 A | 5/1998 | Becnel et al. | 568/328 |
| 5,777,170 A | 7/1998 | Bellani | 568/322 |
| 5,780,495 A | 7/1998 | Del Soldato | 514/413 |
| 5,792,886 A | 8/1998 | Sabahi et al. | 562/466 |
| 5,840,996 A | 11/1998 | Sabahi | 568/634 |
| 5,847,225 A | 12/1998 | Ramachandran et al. | 568/328 |
| 5,861,538 A | 1/1999 | Theriot | 568/313 |
| 5,907,069 A | 5/1999 | Becnel et al. | 568/737 |
| 5,955,635 A | 9/1999 | Cabri et al. | 568/314 |
| 6,057,347 A | 5/2000 | Garvey et al. | 514/364 |

OTHER PUBLICATIONS

Brett, et al., *Nabutemone, Evidence for the Lack of Enterohepatic Circulation of the Active Metabolite 6–MNA in Humans,* Drugs 40 (Suppl. 5), 1990 (pp. 67–70).

Dahl, Stephen L., *Nabumetone: A 'Nonacidic' Nonsteroidal Antiinflammatory Drug,* The Annals of Pharmacology, 27: 456–463 (Apr. 1993).

Harris et al., "Anti–Inflammatory (AI) Efficacy and Acute Gastrointestinal Irritancy (GI) Profile for a Series of Novel 6–Methoxy–2–Naphthylacetic Acid (6–MNA)–Pro–Drugs," *Inflammation Research,* 49(2): S97 (2000).

Hellberg et al., *Novel Esters and Amides of Nonsteroidal Aniinflammatory Carboxylic Acids as Antioxidants and Anitproliferative Agents, J. Med. Chem.,* 42(2): 267–276 (1999).

Hyneck, Martha, *An Overview of the Clinical Pharmacokinetics of Nabumetone, The Journal of Rheumatology,* 19(36): 20–24 (1992).

International Search Report corresponding?to PCT/US 00/29757; date of mailing: Sep. 14, 2001.

International Search Report corresponding to PCT/US 00/41692; Date of Mailing: Oct. 11, 2001.

International Search Report corresponding to PCT/US01/ 10294; Date of Mailing: Apr. 9, 2002.

Jeremy, et al., *Effects of Prodrug Nabumetone, and its Active Metabolite, 6–MNA, on Human and Rat Gastric Mucosal Prostanoids and Platelet Function,* Drugs 40 (Suppl. 5), 1990 (pp. 53–56).

Mangan, et al., *Preclinical Overview of Nabumetone,* The American Journal of Medicine, vol. 83 (suppl. 4B), Oct. 1987 (pp. 6–10).

Nielsen, N. & Bundgaard, H., "Glycolamide Esters as Biolabile Prodrugs of Carboxylic Acid Agents: Synthesis, Stability, Bioconversion, and Physicochemical Properties," *Journal of Pharmaceutical Sciences,* 77(4): 285–298 (1988).

Paris et al., *Glycerides as Prodrugs. 4. Synthesis and Anti-inflammatory Activity of 1,3–dialkanoyl–2–arylaklanoylglycerides,* Eur. J. Med. Chem., 17(2): 193–195 (1982).

Schwenker, G. & Stiefvater, K., "Hydrolysegeschwindigkeit von 5–Acyloxy–1,3–dioxolan–4–onen," *Archiv der Pharmazie,* 324(7): 439–444 (1991).

Soma et al., *Disposition and Excretion of 6–Methoxy–2–Naphthylacetic Acid, the Active Metabolite of Nabumetone in Horses,* AJVR, 57(4): 517–521 (Apr. 1996).

Summers et al., "Hydroxamic Acid Inhibitors of 5–Lipoxygenase: Quantitative Structure–Activity Relationships," *J. Med. Chem.,* 33(3): 992–998 (1990).

Wadhwa, et al., *Glycolamide esters of 6–methoxy–2–napththylacetic acid as potential pro–drugs— Synthetic and spectral studies,* Indian Journal of Chemistry, vol. 34B, May 19995 (pp. 408–415).

Wadwha, L. & Sharma, P., "Glycolamide Esters of 6–Methoxy–2–Naphthylacetic Acid as Potential Prodrugs— Physicochemical Properties, Chemical Stability and Enzymatic Hydrolysis," *International Journal of Pharmaceutics,* 118(1): 31–39 (1995).

6-METHOXY-2-NAPHTHYLACETIC ACID PRODRUGS

RELATED APPLICATION

This application is a divisional of U.S. patent application Ser. No. 10/223,426 entitled 6-Methoxy-2-Naphthylacetic Acid Prodrugs, filed Aug. 19, 2002, which is a divisional of U.S. patent application Ser. No. 09/698,594, filed Oct. 27, 2000, now U.S. Pat. No. 6,436,990 which claims priority to U.S. Provisional Application 60/161,864, filed Oct. 27, 1999, the disclosures of which are incorporated by reference herein in their entireties.

FIELD AND BACKGROUND OF THE INVENTION

The present invention relates to pharmaceutical compositions useful for treatment of inflammation in humans utilizing compounds that are prodrugs of 6-methoxy-2-naphthylacetic acid (hereinafter "6 MNA").

Various naphthalene derivatives are known to be useful for the treatment of inflammation and for various rheumatic and arthritic conditions. For example, Naproxen having the formula (I):

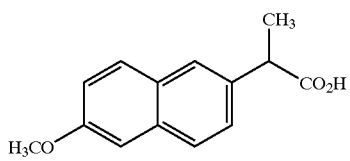

I as described in U.S. Pat. No. 4,009,197 to Fried et al. Compound (I) can, however, cause severe irritation of the gastrointestinal tract at dosages only slightly greater than the excess of the therapeutic dose.

Another naphthalene derivative is nabumetone having the formula (II):

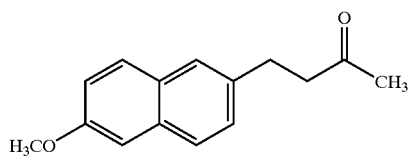

II as described in U.S. Pat. Nos. 4,061,779 and 4,420,639 to Lake et al. Nabumetone works by inhibiting cyclooxygenase, an enzyme responsible for making prostaglandins which are mediators of inflammation. Nabumetone is a prodrug which undergoes hepatic biotransformation to the active component, 6-methoxy-2-naphthylacetic acid, Formula (III):

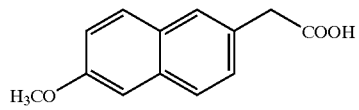

III (See Haddock, R. E. et al; Metabolism of Nabumetone (BRL 14777 by various species including man,"*Xenobiotica;* 14(4): 327–337 (1984)). Nabumetone is commercially available as Relafen® from Smithkline Beecham, Inc. However, only about 35 percent of orally administered nabumetone is transferred in vivo into 6 MNA.

It is therefore an object of the present invention to provide 6 MNA prodrugs which are more readily transformed into 6 MNA than nabumetone. It is believed that improvement in the body's ability to hydrolyze and solubilize the prodrug can contribute to this transformation. Thus, it is another object to improve the hydrolysis and solubility of the prodrug to provide better transformation to 6 MNA.

Another concern with 6 MNA and its related prodrugs is that the presence of the carboxylic acid moiety can cause stomach irritation and/or ulceration. Thus, it is another object of the present invention that provides prodrugs of 6 MNA having a reduced propensity to cause stomach irritation.

SUMMARY OF THE INVENTION

The present invention provides compositions useful for the treatment of inflammation in humans, and related methods of treatment for the same. In one embodiment the composition is

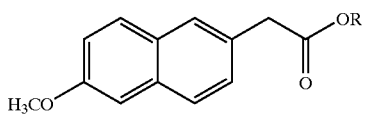

wherein R is selected from the group consisting of $(CH_2)_mO(CH_2)_n$; $(CH_2)_m(OC_2H_4)_pO(CH_2)_n$; $(CH_2)_m(CHOH)_r(CHOH)_s$, and the (R) and (S) enantiomers, and mixtures thereof; and $CH_2COR'$; wherein m is an integer from 2 to 4, n and p are integers from 1 to 4 and r and s are integers from 1 to 2, and R' is selected from the group consisting of $C_1$ to $C_6$ alkyl, $(CH_2)_m O(CH_2)_n$, $CH_2 (OC_2H_4)_pO(CH_2)_n$, and $CH_2 (OC_2H_4)_p$.

In another embodiment, the composition is

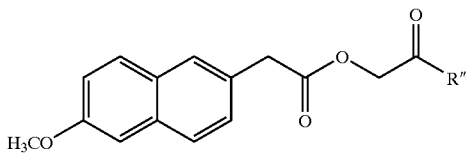

wherein R" is selected from the group consisting of $C_1$ to $C_6$ alkyl, $CH_2 (OC_2H_4)_n O(CH_2)_n$, $CH_2(OC_2H_4)_pOCH_3$, $(OC_2H_4)_n ONO_2$, $(OC_2H_4)_n O(CH_2)_n$, $(CH_2)_n (OC_2H_4)_mONO_2$, $(OC_2H_4)_n O(CH_2)_mOH$, $NH(CH_2)_m (OC_2H_4)_n$, $NH(CH_2)_m (OC_2H_4)_m ONO_2$, $NHO(CH_2)_n CH_3$, $NH(CH_2)_m(OC_2H_4)_pOCH_3$, and $NH(OC_2H_4)_pOCH_3$, wherein m is an integer from 2 to 4, and n and p are integers from 1 to 4.

In yet another embodiment, the composition is

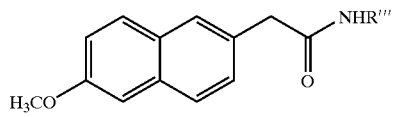

wherein R'" is selected from the group consisting of hydrogen, $O(CH_2)_nCH_3$, $C_1$ to $C_6$ alkyl, $(CH_2)_m (OC_2H_4)_p O(CH_2)_n$, $(CH_2)_m(OC_2H_4)_p$, $(CH_2)_m (OC_2H_4)_n ONO_2$, $(CH_2)_m (OC_2H_4)_p O(CH_2)_mOH$, and $(CH_2)_m NHO(CH_2)_n CH_3$ wherein m is an integer from 2 to 4, and n and p are integers from 1 to 4.

Additional alternative embodiments are R or R" that are therapeutic moieties. Such compositions can be used in methods of treating inflammation.

DETAILED DESCRIPTION OF THE INVENTION

Figure 1:
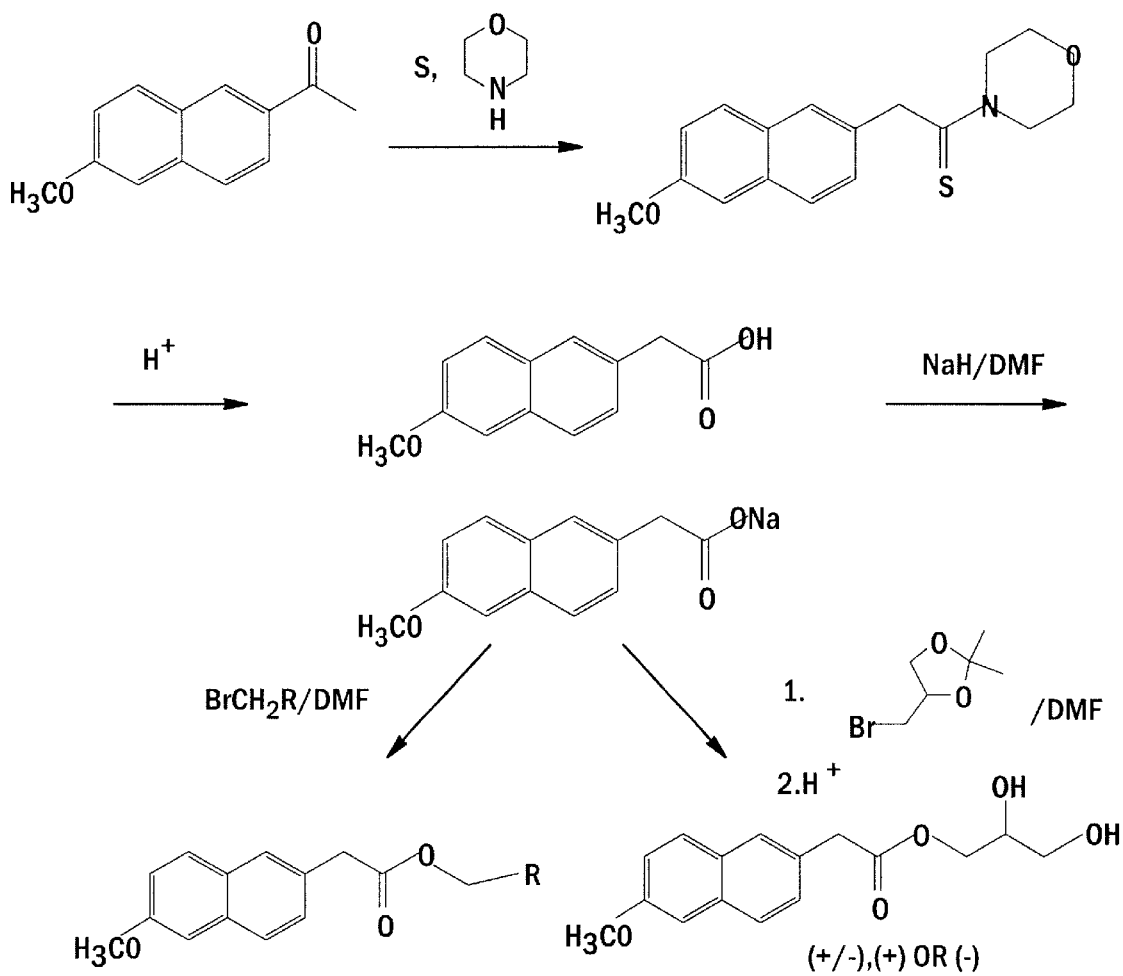
FIGS. 1 and 2 are schematic drawings of pathways for the synthesis of 6 MNA prodrugs of the invention.
Figure 1:
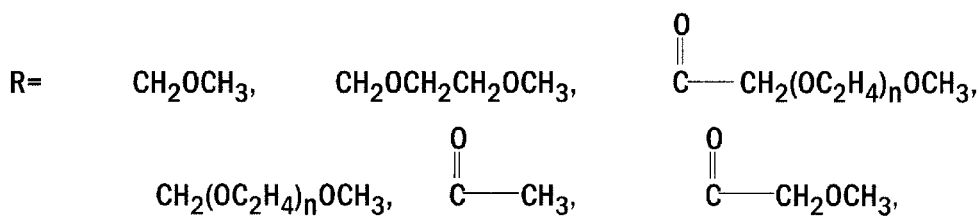

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

A "therapeutically effective amount" is an amount necessary to prevent, delay or reduce the severity of inflammation and also includes an amount necessary to enhance normal physiological functioning.

As used herein, a "pharmaceutically acceptable" component (such as a salt, carrier, excipient or diluent) of a formulation according to the present invention is a component which (1) is compatible with the other ingredients of the formulation in that it can be combined with the 6 MNA prodrugs of the present invention without eliminating the biological activity of the 6 MNA prodrugs; and (2) is suitable for use with an animal (e.g., a human) without undue adverse side effects, such as toxicity, irritation, and allergic response. Side effects are "undue" when their risk outweighs the benefit provided by the pharmaceutical composition.

As discussed above, the present invention provides therapeutically effective amounts of 6 MNA prodrugs. It is believed that the various 6 MNA derivatives provide improved properties over existing compositions. For example, it is believed that the moieties

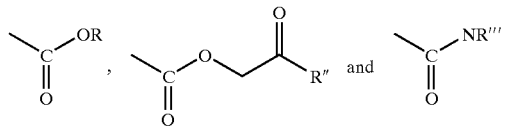

provide improved hydrolysis (and thus improved yield), whereas the R, R" and R'" groups contribute to improved solubility, and improved resistance to ulcers.

Specifically in one embodiment, the pharmaceutical composition is

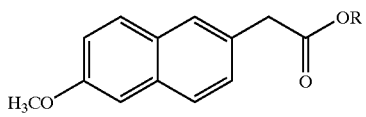

wherein R is selected from the group consisting of $(CH_2)_m O(CH_2)_n$, $(CH_2)_m (OC_2H_4)_p O(CH_2)_n$; $(CH_2)_m (CHOH)_r (CHOH)_s$, and the (R) and (S) enantiomers, and mixtures thereof; and $CH_2COR'$; wherein m is an integer from 2 to 4, n and p are integers from 1 to 4 and r and s are integers from 1 to 2, and R' is selected from the group consisting of $C_1$ to $C_6$ alkyl, $(CH_2)_m O(CH_2)_n$, $CH_2 (OC_2H_4)_p O(CH_2)_n$, and $CH_2 (OC_2H_4)_p$. Specific preferred embodiments are when R is $CH_2CH_2OCH_3$, $CH_2 CH_2 OCH_2 CH_2 OCH_3$, $CHCOCH_2COCH_3$, $CHCOCH_2COCH_3 (OC_2H_4) OCH_3$ and $CHCOCH_2COCH_2OCH_3$.

In another embodiment, the pharmaceutical composition is

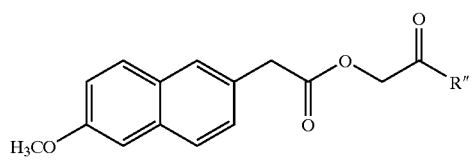

wherein R" is selected from the group consisting of $C_1$ to $C_6$ alkyl, $CH_2 (OC_2H_4)_n O(CH_2)_n$, $CH_2(OC_2H_4)_pOCH_3$, $(OC_2H_4)_n ONO_2$, $(OC_2H_4)_n O(CH_2)_n$, $(CH_2)_n (OC_2H_4)_m ONO_2$, $(OC_2H_4)_n O(CH_2)_m OH$, $NH(CH_2)_m (OC_2H_4)_n$, $NH(CH_2)_m (OC_2H_4)_m ONO_2$, $NHO(CH_2)_n CH_3$, $NH(CH_2)_m(OC_2H_4)_pOCH_3$, and $NH(OC_2H_4)_pOCH_3$, wherein m is an integer from 2 to 4, and n and p are integers from 1 to 4.

In yet another embodiment, the pharmaceutical composition is

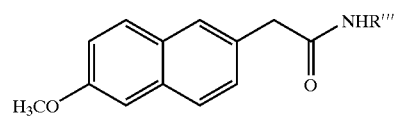

wherein R'" is selected from the group consisting of hydrogen, $O(CH_2)_nCH_3$, $C_1$ to $C_6$ alkyl, $(CH_2)_m (OC_2H_4)_p O(CH_2)_n$, $(CH_2)_m(OC_2H_4)_p$, $(CH_2)_m (OC_2H_4)_n ONO_2$, $(CH_2)_m (OC_2H_4)_pO(CH_2)_mOH$, and $(CH_2)_m NHO(CH_2)_n CH_3$ wherein m is an integer from 2 to 4, and n and p are integers from 1 to 4.

In the above compounds, R and R" can be defined as previously, or can be a therapeutic moiety such as

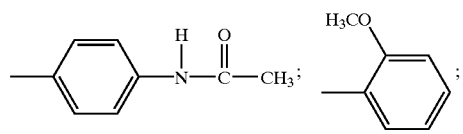

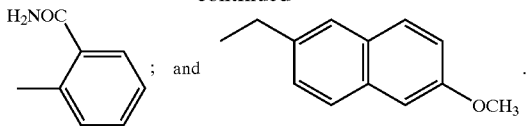

6 MNA prodrugs of the present invention may optionally be administered in conjunction with other compounds useful in the treatment of inflammation or useful in treatment of other indications associated with inflammation such as pain. The other compounds may optionally be administered concurrently. As used herein, the word "concurrently" means sufficiently close in time to produce a combined effect (that is, concurrently may be simultaneously, or it may be two or more events occurring within a short time period before or after each other).

As used herein, the administration of two or more compounds "in combination" means that the two compounds are administered closely enough in time that the presence of one alters the biological effects of the other. The two compounds may be administered simultaneously (i.e., concurrently) or sequentially. Simultaneous administration may be carried out by mixing the compounds prior to administration, or by administering the compounds at the same point in time but at different anatomic sites or using different routes of administration.

The phrases "concurrent administration," "administration in combination," "simultaneous administration" or "administered simultaneously" as used herein, interchangeably mean that the compounds are administered at the same point in time or immediately following one another. In the latter case, the two compounds are administered at times sufficiently close that the results observed are indistinguishable from those achieved when the compounds are administered at the same point in time.

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes.

The 6 MNA prodrugs disclosed herein can, as noted above, be prepared in the form of their pharmaceutically acceptable salts.

Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, malic acid, ascorbic acid, benzoic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

The 6 MNA prodrugs described above may be formulated for administration in a pharmaceutical carrier in accordance with known techniques. See, e.g., Remington, *The Science And Practice of Pharmacy* (9th Ed. 1995). In the manufacture of a pharmaceutical formulation according to the invention, the prodrug (including the physiologically acceptable salts thereof is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the 6 MNA prodrug. One or more 6 MNA prodrugs may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular 6 MNA prodrug which is being used.

Formulations suitable for oral administration may be presented in discrete units, such as capsules, cachets, lozenges, or tables, each containing a predetermined amount of the 6 MNA prodrug; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the 6 MNA prodrug and a suitable carrier (which may contain one or more accessory ingredients as noted above). In general, the formulations of the invention are prepared by uniformly and intimately admixing the 6 MNA prodrug with a liquid or finely divided solid carrier, or both, and then, if necessary, shaping the resulting mixture. For example, a tablet may be prepared by compressing or molding a powder or granules containing the 6 MNA prodrug, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the 6 MNA prodrug in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the 6 MNA prodrug, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the 6 MNA prodrug with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the 6 MNA prodrug. Suitable formulations comprise citrate or bis\tris buffer (pH 6.0) or ethanol/water and contain from 0.1 to 0.2M active ingredient.

The therapeutically effective dosage of any 6 MNA prodrug, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the 6 MNA prodrug, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection. The duration of the treatment is usually once per day for a period of two to three weeks or until the condition is essentially controlled. Lower doses given less frequently can be used prophylactically to prevent or reduce the incidence of recurrence of the infection.

Figure 2:
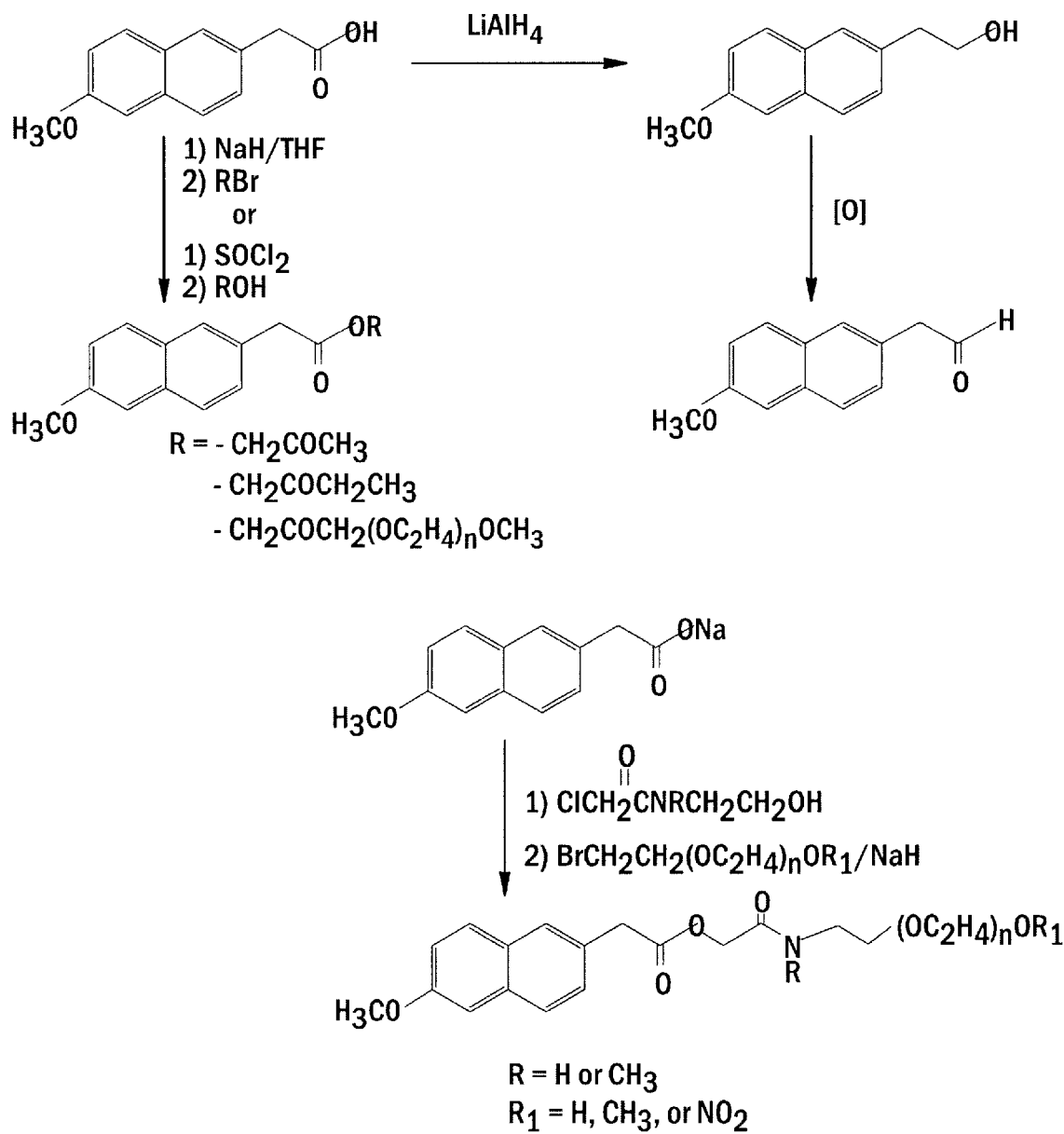

General pathways for synthesizing the compounds of the invention are shown in FIGS. 1 and 2; specific synthesis are described in the non-limiting Examples.

EXAMPLES

Example 1

Synthesis of (6-methoxy-naphthalen-2-yl)-acetic Acid 2-oxo-propyl Ester

In a 100-mL round-bottom flask, 6 MNA (1.00 g, 4.65 mmol) was dissolved in anhydrous DMF (50 ml) and $Na_2CO_3$ (1.08 g, 10.2 mmol) was added with stirring. Chloroacetone (0.407 mL, 5.12 mmol) was added dropwise to the reaction mixture and stirring was continued overnight at room temperature. The DMF was removed under reduced pressure and $CH_2Cl_2$ (75 mL) was added to the remaining residue. The resulting solution was washed with water (3×100 mL) and brine (3×100 mL). The organic layer was dried over $MgSO_4$, filtered, and the solvent removed under reduced pressure to give an off-white solid. Recrystallization from ethyl acetate produced the desired product as off-white crystals in 57.6% yield (0.729 g): mp 122–124° C.; IR (KBr) 2939, 1761, 1731, 1642, 1607, 1513, 1490, 1418, 1395, 1348, 1283, 1236, 1200, 1159, 1053, 1029, 917, 864, 811 $cm^{-1}$; $^1H$ NMR ($CDCl_3$) ∂ 2.11 (s, 3H), 3.88 (s, 2H), 3.91 (s, 3H), 4.66 (s, 2H), 7.12 (s, 1H), 7.15 (d, J=2.7 Hz, 1H), 7.40 (dd, J=1.8, 8.4 Hz, 1H), 7.68 (s, 1H), 7.72 (d, J =3.9 Hz, 2H); FABMS (NBA) m/z 272 $(M)^+$.

Example 2

Synthesis of (6-Methoxy-naphthalen-2-yl)-acetic acid 2-(2-nitrooxy-ethoxy)-ethyl ester In reaction flask #1: NaH (60% suspension in oil, 0.43 g, 0.011 mol) was suspended under nitrogen in anhydrous DMF and 6 MNA (2 g, 0.00926 mol) in anhydrous DMF (60 ml) was added dropwise. Reaction mixture was stirred for 1 hours and cannulated into another reaction flask #2, containing solution of 2-bromoethylether 11.07 g, 0.027 mol in 30 ml of DMF. Reaction mixture was stirred overnight (~17 hours) at room temperature under nitrogen, then 1 h at 40–50° C. Then deionized water was added and the product was extracted with methylene chloride several times, then dried over sodium sulfate, filtered, concentrated via rotovap. Crude material was chromatographed on silica gel column, using ethyl acetate/hexane solvent mixture and then chromatographed, using diethyl ether/hexane solvent system as developing agent. Fractions, containing the product were collected, concentrated, recrystallized and 2.52 g of the compound was analyzed by IR, NMR. (Yield~74%).

Example 3

Synthesis of (6-methoxy-naphthalen-2-yl)-acetic acid carboxymethyl ester

Bromoacetyl bromide (0.432 mL, 4.95 mmol) was dissolved in anhydrous $CH_2Cl_2$ (10 mL) and cooled to 0° C. in an ice bath. Upon addition of triethylamine (0.829 mL, 5.94 mmol) to the solution, a precipitate formed. 2-Trimethylsilylethanol (0.710 mL, 4.95 mmol) was added dropwise with stirring to the reaction solution at O° C. After addition was complete, the reaction was allowed to warm to room temperature and stirred for an additional 20 min. The reaction mixture was placed in a separatory funnel and washed with 1 M HCl (1×50 mL), sat'd $NaHCO_3$ (1×50 mL), and brine (2×50 mL). The organic layer was dried over $MgSO_4$, filtered, and the solvent removed under reduced pressure to give the desired ester as a brown oil (0.736 g, 62.2% yield). IR showed complete conversion to the ester; IR (NaCl): 2952, 2899, 1739, 1627, 1421, 1407, 1360, 1249, 1169, 1112, 1043, 983, 944, 844 $cm^{-1}$; $^1H$ NMR ($CDCl_3$) ∂ 0.017 (d, J=6.9 Hz, 9H), 0.97 (m, 2H), 3.71 (t, J=8.1 Hz, 2H), 4.24 (t,J=8.1 Hz,2H).

In a 50-mL round-bottom flask, 6 MNA (0.602 g, 2.80 mmol) was dissolved in anhydrous DMF (25 ml), and Na$_2$CO$_3$ (0.297 g, 2.80 mmol) was added with stirring. Bromo-acetic acid 2-trimethylsilanyl-ethyl ester prepared above (0.736 mL, 3.08 mmol) was added dropwise to the reaction mixture and stirring was continued overnight at room temperature. The DMF was removed under reduced pressure and CH$_2$Cl$_2$ (60 mL) was added to the remaining residue. The resulting solution was washed with water (3×60 mL) and brine (3×60 mL). The organic layer was dried over MgSO$_4$, filtered, and the solvent removed under reduced pressure to give the desired product as a dark brown oil (0.630 g, 60.3% yield). IR showed complete conversion to the ester; IR (NaCl): 2951, 2892, 1755, 1672, 1637, 1607, 1507, 1490, 1466, 1413, 1389, 1301, 1218, 1159, 1065, 1042, 936, 894, 847 cm$^{-1}$.

In a 50-mL round-bottom flask, the 6 MNA ester prepared above (0.630 g, 2.93 mmol) was dissolved in anhydrous DMF (20 ml) and stirred under a nitrogen atmosphere. The tetrabutylammonium fluoride (1.0M in THF, 1.70 mL, 5.86 mmol) was added dropwise to the reaction mixture over a 2 min period. The reaction mixture continued to stir under an inert atmosphere for an additional 2 h. Dichloromethane (15 mL) and water (10 mL) were added to the reaction mixture and the organic layer was washed with water (3×60 mL), brine (3×60 mL), dried over MgSO$_4$, filtered, and evaporated. The resulting dark oil was purified by column chromatography (SiO$_2$: ethyl acetate/hexanes 1:2 followed by methanol) to give the desired product as a tan solid in 25.0% yield (0.117 g): mp 190–192° C. (dec); IR (KBr) 3310 (br), 2951, 1725, 1602, 1507, 1495, 1431, 1324, 1277, 1224, 1142, 1030, 965, 900, 853, 818 cm$^{-1}$; FABMS (NBA) m/z 274 (M)$^+$.

Example 4
Synthesis of (6-methoxy-naphthalen-2-yl)-acetic acid ethoxycarbonylmethyl ester In a 250-mL round-bottom flask, 6 MNA (3.00 g, 14.0 mmol) was dissolved in anhydrous DMF (100 ml) and Na$_2$CO$_3$ (1.62 g, 15.3 mmol) was added with stirring. Ethylbromoacetate (1.70 mL, 15.3 mmol) was added dropwise to the reaction mixture and stirring was continued overnight at room temperature. The DMF was removed under reduced pressure and CH$_2$Cl$_2$ (100 mL) was added to the remaining residue. The resulting solution was washed with water (3×150 mL) and brine (3×150 mL). The organic layer was dried over MgSO$_4$, filtered, and the solvent removed under reduced pressure to give an off-white solid. Purification by column chromatography (SiO$_2$: ethyl acetate/hexanes 1:2) gave the desired product as an off-white solid in 78.9% yield (3.32 g): mp 38–40° C.; IR (KBr) 2956, 1749, 1637, 1607, 1500, 1484, 1378, 1266, 1236, 1159, 1059, 1024, 953, 912, 853, 811 cm$^{-1}$; $^1$H NMR (CDCl$_3$) $\partial$ 1.23 (t, J=7.2 Hz, 3H), 3.87 (s, 2H), 3.91 (s, 3H), 4.19 (m. 2H), 4.63 (s, 2H), 7.11 (s, 1H), 7.15 (d, J=2.7 Hz, 1H), 7.40 (dd, J=1.8, 8.4 Hz, 1H), 7.68 (s, 1H), 7.71 (d, J =4.5 Hz, 2H); FABMS (NBA) m/z 302 (M)$^+$.

Rat Paw Edema and hydrolysis data are provided data are provided in Tables 1 and 3.

TABLE 1

Rat Paw Edema Results

| Compound | Dose (mg/kg) | % Inhibition | ED$_{50}$ (mg/kg) |
|---|---|---|---|
| Nabumetone | 79.0 | 60 | 35.9 |
| 6-MNA | 75.0 | 45 | |

TABLE 1-continued

Rat Paw Edema Results

| Compound | Dose (mg/kg) | % Inhibition | ED$_{50}$ (mg/kg) |
|---|---|---|---|
| Indomethacin | 10.0 | 51 | |
| Example 1 | 94.3 | 65 | 33.9 |
| Example 2 | 121.0 | 57 | |
| Example 3 | 94.9 | 58 | |
| Example 4 | 121.0 | 38 | |

TABLE 2

Chemical Hydrolysis

| | PH 3 | PH 7.4 | PH 8 |
|---|---|---|---|
| Example 1 | >25 h | 22 h | 7 h |
| Example 2 | >300 h | ~280 h | ~280 h |
| Example 4 | stable for 3 hours | | |

TABLE 3

In Vitro Hydrolysis in Rat Plasma

| | PH 3 |
|---|---|
| Example 1 | 21% conversion to 6-MNA in ~2 h |
| Example 2 | T½> 5 mm |

Example 5
Synthesis of (6-Methoxy-naphthalen-2-yl)-acetic acid 3-nitrooxy-2-oxo-propyl ester In reaction flask #1: NaH(60%suspension in oil, 0.43 g, 0.011 mol) was suspended under nitrogen in anhydrous DMF and 6 MNA(2 g, 0.00926 mol) was added dropwise. Reaction mixture was stirred for 2 hours and cannulated into another reaction flask #2, containing solution of dibromoacetone 7.9 g, 0.0379 mol in DMF. Reaction mixture was stirred overnight (~17 hours) and TLC was checked. Then deionized water was added and the product was extracted with methylene chloride several times, then dried over sodium sulfate, filtered and concentrated. Crude material was chromatographed on silica gel column, using ethyl acetate/hexane solvent mixture and then chromatographed, using diethyl ether/hexane solvent system as developing agent. Fractions, containing the product were collected, concentrated, recrystallized and compound was analyzed by MS. The compound contained one bromine atom; that's why it has an M+2 peak almost equal in intensity to the molecular ion (because of the presence of a molecular ion containing the 81 Br isotope) Mass spectrometry, 350.8 and 352.8.

1.71 mg, 0.203 mmol of this compound was dissolved in acetonitrile (15 ml) and silver nitrate 79.5 mg, 0.468 mmol solution in 2 ml of acetonitrile added. The reaction mixture was stirred at 80° C. at the dark and then filtered. From a resulting solution, the solvent was evaporated at a reduced pressure, and a residue was obtained to which methylene chloride was added. Then the precipitate was filtered off and methylene chloride phase was concentrated, passed thorough a silica gel column, using diethyl ether/hexane and then recrystallysed, washed with hexane and dried via vacuum to obtain the final product. The final product was analyzed by elemental analysis, IR, MS, NMR.

Example 6
Synthesis of (6-methoxy-naphthaleon-2-yl)-acetic acid 2-(2-methoxy-ethoxy)-ethyl ester In a 10-mL round-bottom flask, 6 MNA (1.00 g, 4.63 mmol) was suspended in oxalyl chloride (7 mL) and the reaction mixture was stirred at room temperature for 1 h during which time the 6 MNA dissolved. The oxalyl chloride was removed by vacuum distillation to yield the 6 MNA acid chloride (2.18 g, 100% yield) as a red solid. IR showed complete conversion to the acid chloride; IR (KBr): 3061, 3020, 2949, 2901, 2831, 1800, 1605, 1493, 1393, 1275, 1234, 1128, 1028, 951, 869 $cm^{-1}$; mp 80–82° C.

Diethylene glycol monomethyl ether (1.22 g, 10.2 mmol) was dissolved in anhydrous $CH_2Cl_2$ (20 mL) and added dropwise to a suspension of NaH (60% in mineral oil, 0.407 g, 10.2 mmol) in anhydrous $CH_2Cl_2$ (10 mL) at 0° C. The reaction mixture was allowed to warm to room temperature for and stirred for 2 h at which time 6 MNA acid chloride (1.08 g, 4.63 mmol) in anhydrous $CH_2Cl_2$ (50 mL) was added. The resulting reaction mixture was stirred at room temperature overnight. The reaction mixture was transferred to a separatory funnel and washed with water (2×100 mL) and brine (2×100 mL). The organic layer was dried over $MgSO_4$, filtered, and the solvent removed under reduced pressure to give an orange oil. Purification by column chromatography ($SiO_2$: ethyl acetate/hexanes 2:1) gave the desired product as an oil in 69.3% yield (1.11 g): IR (NaCl) 2939, 2892, 1737, 1636, 1607, 1483, 1454, 1389, 1224, 1035, 858 $cm^{-1}$; FABMS (NBA) m/z 318 $(M+H)^+$.

Example 7
Synthesis of (6-methoxy-naphthalen-2-yl)-acetic acid 2-methoxy-phenyl ester In a 10-mL round-bottom flask, 6 MNA (1.50 g, 6.94 mmol) was suspended in oxalyl chloride (7 mL) and the reaction mixture was stirred at room temperature for 3 h during which time the 6 MNA dissolved. The oxalyl chloride was removed by vacuum distillation to yield the 6 MNA acid chloride (1.63 g, 100% yield) as a red solid. IR showed complete conversion to the acid chloride; IR (KBr): 3061, 3020, 2949, 2901, 2831, 1800, 1605, 1493, 1393, 1275, 1234, 1128, 1028, 951, 869 $cm^{-1}$; mp 80–82° C.

Guaiacol (0.840 mL, 7.64 mmol) was dissolved in anhydrous DMF (30 mL) and added dropwise to a suspension of NaH (60% in mineral oil, 0.304 g, 7.64 mmol) in anhydrous DMF (10 mL). The reaction mixture was stirred at room temperature for 1.5 h at which time 6 MNA acid chloride (1.63 g, 7.64 mmol) in anhydrous DMF (10 mL) was added. The resulting reaction mixture was stirred at room temperature overnight. The DMF was removed under reduced pressure and $CH_2Cl_2$ (50 mL) was added to the remaining residue. The resulting solution was washed with water (2×50 mL) and brine (2×50 mL). The organic layer was dried over $MgSO_4$, filtered, and the solvent removed under reduced pressure to give a dark oil. Purification by column chromatography ($SiO_2$: ethyl acetate/hexanes 1-:2) gave the desired product as an oil which was precipitated by addition of diethyl ether (0.800 g, 35.8% yield): mp 90.5–92.5° C.; IR (KBr) 3060, 2966, 2936, 2836, 1757, 1609, 1506, 1463, 1392, 1311, 1267, 1224, 1115, 1028, 952, 854 $cm^{-1}$; FABMS (NBA) m/z 322 $(M+H)^+$.

Example 8
Synthesis of N-(2-methoxy-ethyl)-2-(6-methoxy-naphthalen-2-yl)-acetamide The 6 MNA acid chloride (1.50 g, 6.8 mmol) and 2-methoxyethylamine was dissolved in anhydrous THF (10 mL). Then triethylamine was added and a precipitate immediately formed. The reaction mixture was stirred overnight at room temperature. The crude reaction mixture was dissolved in $CH_2Cl_2$ (50 mL), washed, $H_2O$ (50 mL), sa. $NaHCO_3$ (2×40 mL), $H_2O$ (50 mL), dried ($MgSo_4$), and evaporated to dryness. The crude product was then recrystallized from $CH_2Cl_2$/hexanes to afford tan crystals (0.853 g, 48% yield): mp 129° C.; IR (NaCl) 3237 (br), 3065, 2886, 1633, 1613, 1575, 1493, 1460, 1394, 1275, 1229, 1129, 857, 811 $cm^{-1}$; $^1$H NMR ($CDCl_3$) $\partial$ 3.26 (s, 3H), 3.97 (m, 4H), 3.70 (s, 2H), 3.93 (s, 3H), 7.14 (m, 2H), 7.18 (d, J=2.4 Hz, 1H), 7.34 (dd, J=1.5, 8.7 Hz, 1H), 7.69 (m, 3H); FABMS (NBA) m/z 274 $(m+H)^+$.

Example 9
Synthesis of [2-(6-methoxy-naphthalen-2-yl)-acetoamino]-acetic acid methyl ester In a 10-mL round-bottom flask, 6 MNA (1.08 g, 5.02 mmol) was suspended in thionyl chloride (7 mL) and the reaction mixture was stirred at room temperature for 1 h during which time the 6 MNA dissolved. The Thionyl chloride was removed by vacuum distillation to yield the 6 MNA acid chloride (1.18 g, 100% yield) as a red solid. IR showed complete conversion to the acid chloride; IR (KBr): 3061, 3020, 2949, 2901, 2831, 1800, 1605, 1493, 1393, 1275, 1234, 1128, 1028, 951, 869 $cm^{-1}$; mp 80–82° C.

The 6 MNA acid chloride (1.18 g, 5.02 mmol) was dissolved in anhydrous DMF (20 ml) and added dropwise to a stirring solution of glycine methyl ester hydrochloride (0.633 g, 5.04 mmol) and triethylamine (1.55 mL, 11.1 mmol) in anhydrous DMF (10 mL). The reaction mixture was stirred at room temperature under a nitrogen atmosphere overnight. The DMF was removed under reduced pressure and $CH_2Cl_2$ (40 mL) was added to the remaining residue. The resulting solution was washed with water (3×60 mL) and brine (3×60 mL). The organic layer was dried over $MgSO_4$, filtered, and the solvent removed under reduced pressure to give a brown solid. Purification by column chromatography (SiO2: ethyl acetate) gave the desired product as an off-white solid in 30.6% yield (0.441 g): mp 118–120° C.; IR (KBr) 3222, 3062, 2951, 1739, 1640, 1573, 1441, 1381, 1266, 1215, 1171, 1043, 997, 894, 853 $cm^{-1}$; FABMS (NBA) m/z 288 $(M)^+$.

Example 10
Synthesis of 2-(6-methoxy-naphthalen-2-yl)-acetamide

In a 10-mL round-bottom flask, 6 MNA (1.84 g, 8.56 mmol) was suspended in oxalyl chloride (7 mL) and the reaction mixture was stirred at room temperature for 3 h during which time the 6 MNA dissolved. The oxalyl chloride was removed by vacuum distillation to yield the 6 MNA acid chloride (2.00 g, 100% yield) as a red solid. IR showed complete conversion to the acid chloride; IR (KBr): 3061, 3020, 2949, 2901, 2831, 1800, 1605, 1493, 1393, 1275, 1234, 1128, 1028, 951, 869 $cm^{-1}$; mp 80–82° C.

The 6 MNA acid chloride (2.00 g, 8.56 mmol) was dissolved in anhydrous DMF (20 ml) and cooled to 0° C. in an ice bath. Ammonia (0.5M in dioxane, 34.2 mL, 17.1 mmol) was added dropwise to the acid chloride solution with stirring. Care was taken to keep the reaction temperature at 0° C. Upon complete addition, the reaction mixture was allowed to warm to room temperature and continued to stir overnight. Water (20 mL) and ethyl acetate (20 mL) were added after which a precipitate formed. The solid was collected by suction filtration and recrystallization from ethanol produced the desired product as a tan solid in 65.4% yield (1.20 g): mp 234–236° C.; IR (KBr) 3364, 3171, 1640, 1490, 1414, 1235, 1162, 1030, 857 $cm^{-1}$; FABMS (NBA) m/z 216 $(M+H)^+$.

The foregoing is illustrative of the present invention and is not to be construed as limiting thereof. The invention is defined by the following claims, with equivalents of the claims to be included therein.

That which is claimed is:

1. A pharmaceutical composition comprising a therapeutically effective amount of a compound of the formula:

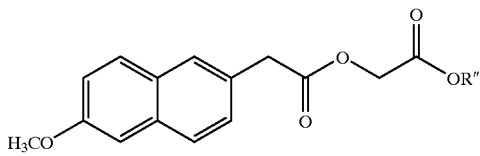

wherein R" is a therapeutic moiety selected from the group consisting of;

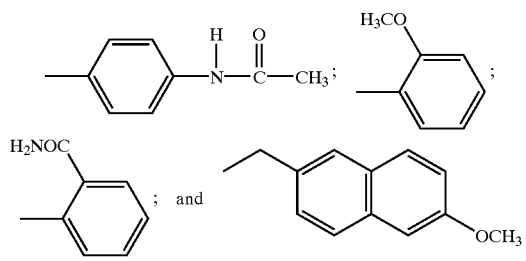

or a pharmaceutically acceptable salt thereof.

2. The pharmaceutical composition according to claim 1, wherein R" is:

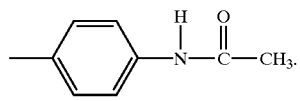

3. The pharmaceutical composition according to claim 1, wherein R" is:

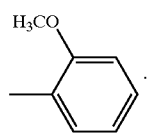

4. The pharmaceutical composition according to claim 1, wherein R" is:

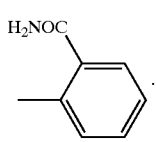

5. The pharmaceutical composition according to claim 1, wherein R" is:

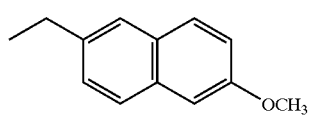

6. The pharmaceutical composition according to claim 1, wherein the pharmaceutical composition is useful for treating inflammation in human or animal subjects.

7. The pharmaceutical composition according to claim 1, wherein the pharmaceutical composition is suitable for oral administration.

8. The pharmaceutical composition according to claim 1, wherein the pharmaceutical composition is suitable for parenteral administration.

9. The pharmaceutical composition according to claim 1, further comprising at least one other compound useful in the treatment of inflammation in human or animal subjects.

10. The pharmaceutical composition according to claim 1, further comprising at least one pharmaceutically acceptable carrier, diluent, or excipient.

11. A pharmaceutical formulation comprising:

a therapeutically effective amount of a compound of the formula:

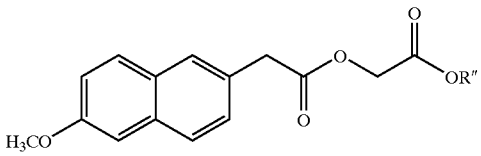

wherein R" is a therapeutic moiety selected from the group consisting of;

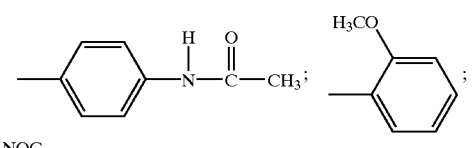

or a pharmaceutically acceptable salt thereof; and at least one pharmaceutically acceptable carrier, diluent, or excipient.

12. The pharmaceutical formulation according to claim 1, wherein R" is:

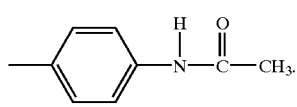

13. The pharmaceutical formulation according to claim 11, wherein R" is:

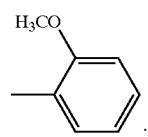

14. The pharmaceutical formulation according to claim 11, wherein R" is:

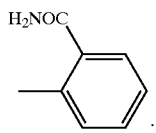

15. The pharmaceutical formulation according to claim 11, wherein R" is:

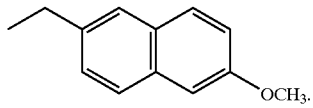

16. A pharmaceutical formulation comprising:
a therapeutically effective amount of a compound of the formula:

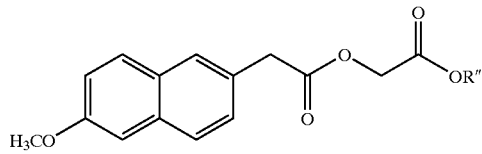

wherein R" is a therapeutic moiety selected from the group consisting of;

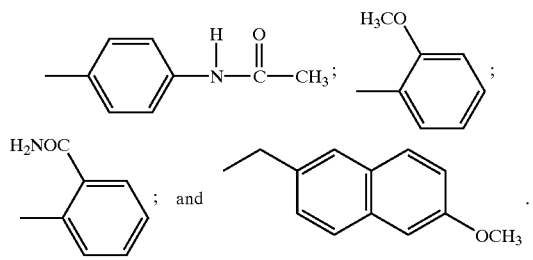

or a pharmaceutically acceptable salt thereof;

at least one other compound useful in the treatment of inflammation; and at least one pharmaceutically acceptable carrier, diluent, or excipient.

17. The pharmaceutical formulation according to claim 16, wherein R" is:

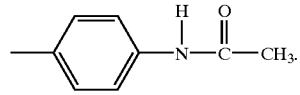

18. The pharmaceutical formulation according to claim 16, wherein R" is:

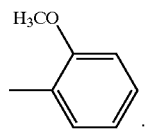

19. The pharmaceutical formulation according to claim 16, wherein R" is:

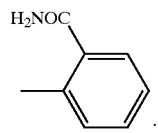

20. The pharmaceutical formulation according to claim 16, wherein R" is:

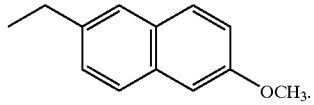

* * * * *

UNITED STATES PATENT AND TRADEMARK OFFICE
CERTIFICATE OF CORRECTION

PATENT NO.     : 6,610,739 B2
DATED          : August 26, 2003
INVENTOR(S)    : Ekwuribe et al.

It is certified that error appears in the above-identified patent and that said Letters Patent is hereby corrected as shown below:

Column 14,
Line 50, should read -- 12. The pharmaceutical formulation according to claim 11, --

Signed and Sealed this

Sixth Day of April, 2004

JON W. DUDAS
*Acting Director of the United States Patent and Trademark Office*